United States Patent
Rees-Jones et al.

(10) Patent No.: US 12,195,893 B2
(45) Date of Patent: Jan. 14, 2025

(54) FABRICS, COMPRESSION GARMENTS AND COMPRESSION GARMENT SYSTEMS

(71) Applicant: THE MERINO COMPANY LIMITED, Auckland (NZ)

(72) Inventors: Blythe Guy Rees-Jones, Papamoa (NZ); Rogier Rolf Simons, Mt Maunganui (NZ); Stewart Roger Collie, Upper Riccarton (NZ); Marie Stella Banks, Normanale (NZ)

(73) Assignee: THE MERINO COMPANY LIMITED, Auckland (NZ)

( * ) Notice: Subject to any disclaimer, the term of this patent is extended or adjusted under 35 U.S.C. 154(b) by 438 days.

(21) Appl. No.: 15/450,735

(22) Filed: Mar. 6, 2017

(65) Prior Publication Data
US 2017/0175310 A1    Jun. 22, 2017

Related U.S. Application Data

(63) Continuation of application No. 13/393,379, filed on Feb. 29, 2012, now abandoned.

(51) Int. Cl.
*D04B 1/26* (2006.01)
*A61F 13/08* (2006.01)

(52) U.S. Cl.
CPC ............ *D04B 1/265* (2013.01); *A61F 13/085* (2013.01); *D10B 2401/02* (2013.01)

(58) Field of Classification Search
CPC ............ A41D 2400/38; A41D 13/0015; A41D 13/1209; A41D 27/10; A41D 7/00;
(Continued)

(56) References Cited

U.S. PATENT DOCUMENTS 3,250,095 A     5/1966   Bird
3,538,914 A *  11/1970   Myers ................... A61F 13/085
                                                          450/142
(Continued)

FOREIGN PATENT DOCUMENTS

DE      3633598       4/1988
DE      3705335       9/1988
(Continued)

OTHER PUBLICATIONS

Communication pursuant to Article 94(3) EPC, Aug. 9, 2018.
(Continued)

*Primary Examiner* — Alissa J Tompkins
*Assistant Examiner* — Catherine M Ferreira
(74) *Attorney, Agent, or Firm* — Conley Rose, P.C.

(57) ABSTRACT

Various fabrics, compression garments and compression garment systems are described. Fabrics formed from wicking and absorbent materials provide effective compression and an improved environment next to a wearer's skin, which provides greater comfort and improved overall performance. Two and multi-layer compression garments are described. An outer layer may be formed with an opening having a closure and an elastic material joining the sides of the opening. This provides a first level of compression with the closure open and a second level of compression with the closure closed and also helps a user in applying the garment.

19 Claims, 8 Drawing Sheets

(58) Field of Classification Search
CPC .. A41D 13/0543; A41D 13/129; A41D 15/04; A41D 1/22; A41D 2400/22; A41D 27/245; A41D 31/0005; A41D 31/02; A41D 3/00; A41D 2400/32; D04B 1/265; A61F 13/085; D10B 2401/02
USPC .............................. 2/69, 239, 240, 241, 242
See application file for complete search history.

(56) References Cited

U.S. PATENT DOCUMENTS

| | | | |
|---|---|---|---|
| 4,015,296 | A | 4/1977 | Malick |
| 4,166,463 | A | 9/1979 | Bloom |
| 4,207,885 | A | 6/1980 | Hampton et al. |
| 4,502,301 | A | 3/1985 | Swallow et al. |
| 4,562,114 | A | 12/1985 | Sawanishi et al. |
| 4,665,909 | A | 5/1987 | Trainor |
| 5,195,950 | A | 3/1993 | Delannoy |
| 5,319,807 | A | 6/1994 | Brier |
| 6,012,177 | A | 1/2000 | Cortinovis |
| 6,050,967 | A | 4/2000 | Walker et al. |
| 6,135,974 | A | 10/2000 | Matz |
| 6,308,337 | B1 | 10/2001 | Penley |
| 6,338,723 | B1 | 1/2002 | Carpenter et al. |
| 6,371,933 | B1 | 4/2002 | Mollard |
| 6,488,645 | B1 | 12/2002 | Reinhard |
| 6,523,729 | B1* | 2/2003 | Gardon-Mollard ........................ A47G 25/907 223/112 |
| 6,613,007 | B1* | 9/2003 | Reid, Jr. ................. A61F 13/08 602/62 |
| 6,684,412 | B2 | 2/2004 | Ricci et al. |
| 6,725,691 | B2 | 4/2004 | Yakopson |
| 7,135,007 | B2 | 11/2006 | Scott et al. |
| 7,434,423 | B1 | 10/2008 | Reid, Jr. |
| 7,473,816 | B2 | 1/2009 | Hall |
| 8,075,507 | B2 | 12/2011 | Linnane |
| 8,510,972 | B2* | 8/2013 | Bizzo ................... A43C 11/002 36/50.1 |
| 2002/0172181 | A1* | 11/2002 | Sayeed .................. H01Q 1/246 370/335 |
| 2003/0135171 | A1 | 7/2003 | Ingram et al. |
| 2003/0195449 | A1 | 10/2003 | Coleman |
| 2004/0214495 | A1* | 10/2004 | Foss ...................... B32B 27/306 442/364 |
| 2005/0010155 | A1 | 1/2005 | Chiang et al. |
| 2006/0156456 | A1* | 7/2006 | Teixeira ............... A41B 11/006 2/239 |
| 2008/0071204 | A1* | 3/2008 | Linnane .................. A61F 13/08 601/151 |
| 2008/0286513 | A1 | 11/2008 | Haigh et al. |
| 2009/0024069 | A1 | 1/2009 | Appel |
| 2009/0301139 | A1 | 12/2009 | Kolmes |

FOREIGN PATENT DOCUMENTS

| | | |
|---|---|---|
| EP | 1210924 | 6/2002 |
| EP | 1645255 | 4/2006 |
| EP | 1980231 | 6/2010 |
| FR | 2619709 | 3/1989 |
| NZ | 522202 | 1/2005 |
| WO | WO-2005/094738 | 10/2005 |
| WO | WO-2008006227 | 1/2008 |
| WO | WO-2008/116791 | 10/2008 |

OTHER PUBLICATIONS

Levana Textiles Limited, Further Examination Report, equivalent PCT application PCT/NZ2010/000173, May 21, 2013.
Search Report in EP Application No. 10812383.7 dated Apr. 30, 2015.
Carolon, Health Support Brochure, (pre Sep. 8, 2009).
Hampton, et al. "A new method of compression therapy in treatment of venous leg ulceration," (pre Sep. 8, 2009).
Jobst, "Medical LegWear", Packaging and Manual, (pre Sep. 8, 2009).
Levana Textiles Limited, et al., PCT Search report mailed Jan. 20, 2011; PCT/NZ2010/000173.

* cited by examiner

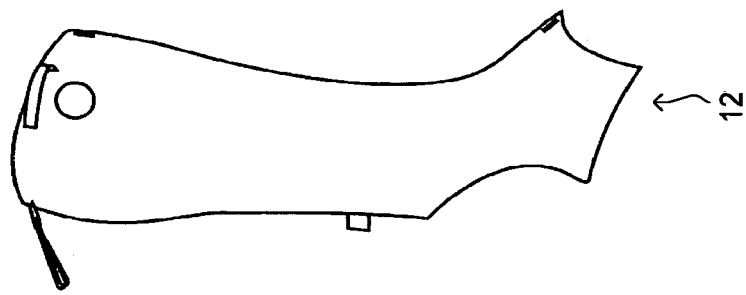
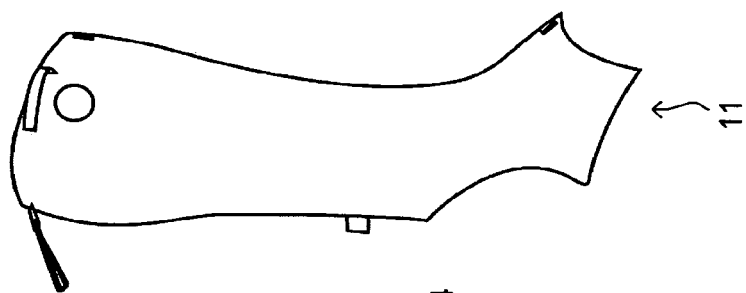
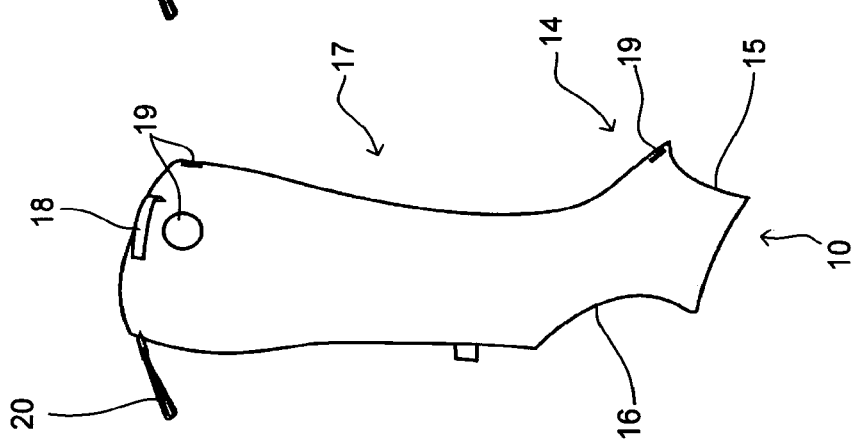
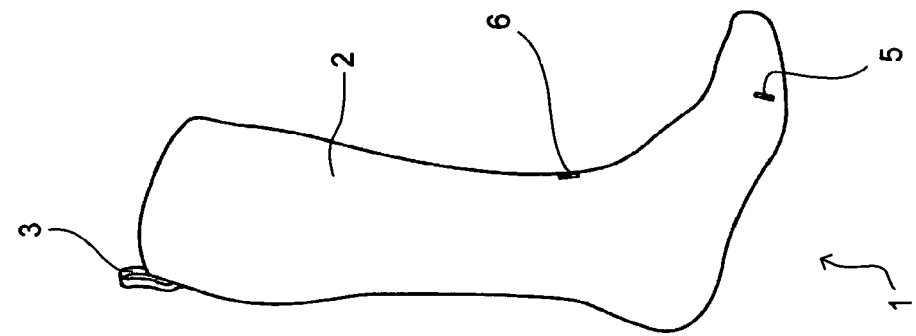

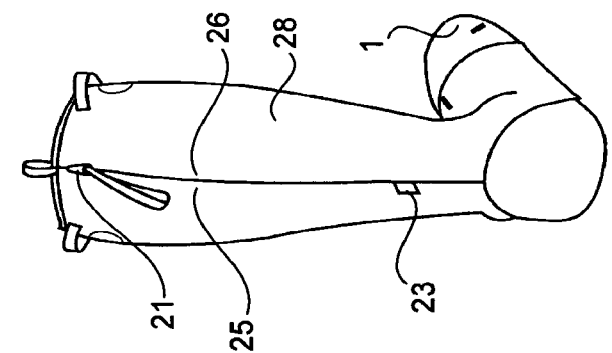
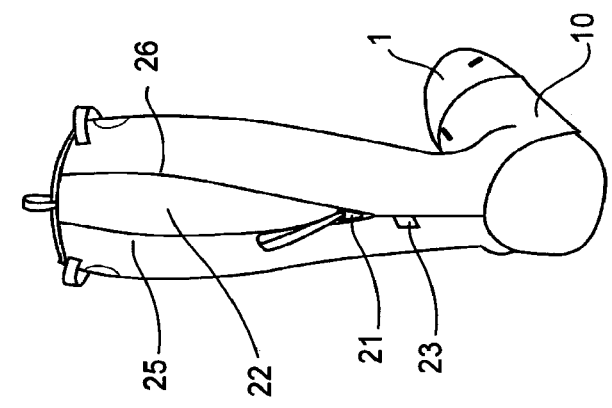
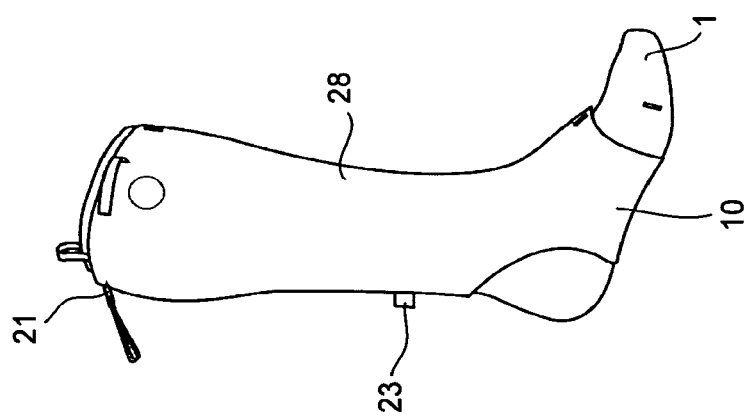
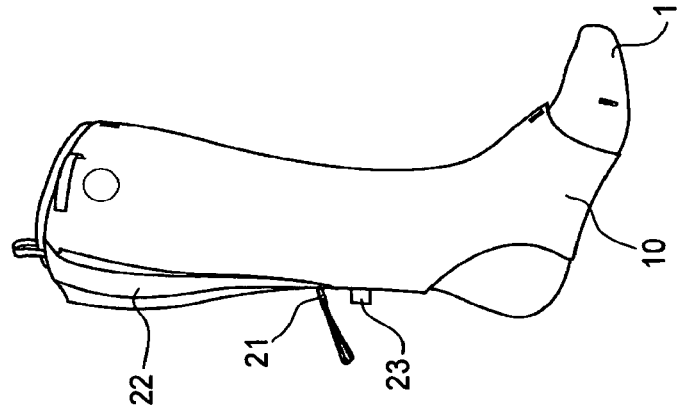

FABRICS, COMPRESSION GARMENTS AND COMPRESSION GARMENT SYSTEMS

CROSS-REFERENCE TO RELATED APPLICATION

This application is a continuation of pending U.S. patent application Ser. No. 13/393,379 filed Feb. 29, 2012 entitled "Fabrics, Compression Garments and Compression Garment Systems"

FIELD OF THE INVENTION

The invention relates generally to fabrics, fabrics for compression therapy and compression garments formed from fabric.

BACKGROUND TO THE INVENTION

Compression therapy is used for treatment or preventative therapy associated with circulatory problems, in particular with vascular disorders in the limbs, especially in the legs. Compression can assist with treatment or prevention of venous ulcers, embolism, oedema, thrombosis, deep vein thrombosis, varicose veins and other venous insufficiencies. Compression therapy is often used by older patients, by those with other health problems such as diabetes or with poor venous blood flow for whatever reason.

Compression is usually measured by pressure applied (in mmHg) or by a class system related to pressure. One class system defines: Class A compression as 10 to 15 mmHg; Class 1 compression as 16 to 21 mmHg; Class 2 compression as 22 to 30 mmHg; Class 3 compression as 34 to 46 mmHg and Class 4 compression as more than 46 mmHg. Where pressure classes are referred to in this specification it is this system that is referenced.

Compression may be applied by one or more elastic bandages wrapped tightly around the patient's limb. Applying these bandages is difficult and they are usually applied by a healthcare worker, not by the patient. In addition to the difficulty for older patients in simply applying a bandage, some strength is required to achieve the necessary compression particularly where a higher level of compression is required. This problem is exacerbated by the facts that bandages need to be changed often and when applied to the limb have a tendency to slip or gradually loosen (resulting in lower pressure); and bandages can be applied incorrectly (e.g. too tightly) which can lead to significant health issues.

It is also difficult to apply bandages to achieve a desired variation of the level of compression along the patient's limb. Typically the level of compression should be greatest at the extremities of the limb and fall gradually along the length of the limb. However, it is difficult to provide the correct variation by manual application of a bandage. Some compression bandages are marked with a scale which provides a rough indication of how far the bandage has been stretched and therefore some idea of the level of compression applied. However, this is a clumsy and unreliable system which relies on user skill in applying the bandage and correct interpretation of the scale.

Compression stockings are also known. These are usually simply tubular elastic bandages which can be pulled on like a sock. Most provide an undesirable variation in compression, since their diameter is simply uniform along the length of the stocking and this shape does not match the variation in the shape of the limb. Some shaped garments are known, but these are still difficult for patients to apply.

Compression stockings are typically formed predominantly from a synthetic material and may include an elastic material to provide the necessary compression.

Existing compression stockings do not provide an optimal environment near the user's skin. In addition to requiring compression to treat underlying vascular disorders, patients often have wounds in their skin (typically ulcers) which must heal. The Applicant has found that existing compression stockings slow or prevent healing, or even contribute to development of further wounds or undesirable skin conditions, by adversely affecting the microenvironment around the wearer's skin. Such adverse effects include promoting excessive moisture or heat as well as physical irritation of the skin.

Compression bandages or garments must be worn routinely over a long period of time to have any benefit. Compression bandages or garments which are uncomfortable because of poor design, incorrect application or undesirable effects on the user's skin environment are therefore particularly problematic.

It is an object of the invention to provide an improved fabric and/or improved compression garment and/or improved compression garment system, or at least to provide the public with a useful choice.

SUMMARY OF THE INVENTION

In a first aspect the invention provides a compression garment formed as a single fabric layer, including: a moisture absorbent material forming at least predominantly an inner surface of the single fabric layer; and a wicking material forming at least predominantly an outer surface of the single fabric layer; wherein the single fabric layer is knitted or woven from threads of at least the first and second materials.

Preferably the moisture absorbent material is composed of fibres having a hydrophilic core and a hydrophobic surface.

Preferably the moisture absorbent material is also a temperature regulating material.

Preferably the moisture absorbent material is also an odour-inhibiting material.

Preferably the moisture absorbent material is also an anti-microbial material.

Preferably the moisture absorbent material is a natural material. Preferably the natural material is wool. Preferably the natural material is merino wool.

Preferably the moisture absorbent material has an average fibre diameter in the range 13 to 23 µm.

Preferably the moisture absorbent material is configured to regulate the skin environment of a wearer.

Preferably the wicking material is composed of fibres having a hydrophilic surface and low moisture absorption.

Preferably the wicking material is an abrasion resistant material.

Preferably the wicking material is a synthetic material. Preferably the wicking material is polyester, nylon or polypropylene.

Preferably the ratio of absorbent material to wicking material by weight is in the range 1:3 to 3:1.

Preferably the single fabric layer includes an elastic material providing or contributing to a compression force provided by the compression garment in use.

Preferably the elastic material is in the form of elastic thread. Preferably the elastic material is elastane.

Preferably the elastic material is contained within the single fabric layer without being exposed on either the inner or outer surface.

Preferably the elastic material forms up to 50% of the weight of the single fabric layer.

Preferably a compression force provided by the garment in use is graduated along the length of the garment.

Preferably the single fabric layer is knitted from threads of at least the first and second materials. Preferably the single fabric layer is knitted as a flat fabric layer. Alternatively the single fabric layer may be formed by an integral knitting process.

Preferably the inner surface is formed by a first set of knit stitches formed at least predominantly from the moisture absorbent material and the outer surface is formed by a second set of knit stitches formed at least predominantly from the wicking material.

Preferably a set of tuck stitches links the knit stitches.

Preferably one or more handles or loops are provided to assist with application of the garment and/or with closing and/or opening of the closure.

Preferably one or more touch markers are positioned and arranged to assist correct alignment of the garment.

In a second aspect the invention provides a method of forming a compression garment, including: providing: first threads formed of an absorbent material; and second threads formed of a wicking material; and processing the first and second threads to form a single fabric layer, in which a first surface is formed at least predominantly by the first threads and a second surface opposing the first surface is formed at least predominantly by the second threads.

Preferably the first and second threads are provided in proportions such that the ratio of absorbent material to wicking material by weight is in the range 1:3 to 3:1.

Preferably third threads of an elastic material are also provided and the first, second and third threads are processed to form the single fabric layer.

Preferably the method includes processing the first, second and third threads such that the elastic material is contained within the single fabric layer without being exposed on either the first or second surface.

Preferably the method includes providing the third threads in proportion such that the elastic material forms up to 50% of the weight of the single fabric layer.

Preferably the method includes shaping and/or varying construction of the single fabric layer such that a compression force provided by the garment in use is graduated along the length of the garment.

Preferably the processing step is a knitting step. Preferably the method includes knitting the single fabric layer as a flat fabric layer. Alternatively the method may include knitting the single fabric layer using an integral knitting process.

Preferably the method includes forming a first set of knit stitches at least predominantly from the moisture absorbent material, the first set of stitches providing the first surface; and forming a second set of knit stitches at least predominantly from the wicking material, the second set of stitches providing the second surface.

Preferably the method includes forming a set of tuck stitches linking the knit stitches.

In a third aspect the invention provides a compression garment including: a shaped fabric body; an opening extending over at least a part of the fabric body; an elastic material connected at both sides of the opening such that, in use, the elastic material tends to draw the sides of the opening together; and a closure configured to close the opening.

Preferably the opening extends to an edge of the fabric body.

Preferably the compression garment provides, in use, a first predetermined level of compression when the opening is closed and a second predetermined level of compression when the opening is open. Preferably the first level is greater than the second level.

Preferably, in use, a circumference of the garment in the region of the opening is reduced by closing the opening with the closure.

Preferably the elastic material is configured to contract so as to lie flat underneath the shaped fabric body when, in use, the opening is closed.

Preferably the closure provides a fixed connection between the sides of the opening when the opening is closed.

Preferably the closure is a zip closure. Alternatively, the closure may include one or more of: hook and loop fasteners, domes, snap fasteners, buckles and/or releasable adhesive.

Preferably the shaped fabric body is shaped to conform to the shape of a wearer's lower leg.

Preferably the opening is positioned to extend along the length of a wearer's leg.

Preferably a lower portion of the garment is configured to fit around a wearer's foot and an upper portion provides the opening, elastic material and closure.

Preferably one or more handles or loops are provided to assist with application of the garment and/or with closing and/or opening of the closure.

Preferably one or more touch markers are positioned and arranged to assist correct alignment of the garment.

In a further aspect the invention provides a multilayer compression garment system including: an inner fabric compression layer configured, in use, to apply a first predetermined level of compression; and an outer fabric compression layer configured, in use, to apply a second predetermined level of compression; wherein the inner layer includes a moisture absorbent material and a wicking material and the outer layer includes a wicking material.

Preferably, in use: moisture vapour in a wearer's skin environment is absorbed by the moisture absorbent material in the inner layer; absorbed moisture in the moisture absorbent material in the inner layer is released towards the exterior of the inner layer; liquid moisture in the skin environment is wicked through the inner layer by the wicking material in the inner layer to the interface between the inner and outer layers; and liquid moisture at the interface is wicked into the outer layer by the second material in the outer layer.

Preferably the compression garment system is a two-layer compression garment system.

Preferably the inner layer is a compression stocking. Preferably the inner layer is a compression garment according to the first aspect above.

Preferably the first predetermined level of compression is in the range 5 to 22 mmHg. More preferably the first predetermined level of compression is in the range 10 to 15 mmHg.

Preferably the outer surface of the inner layer has a low fabric-to-fabric coefficient of friction to ease application of the outer layer over the inner layer.

Preferably the outer layer also includes a moisture absorbent material.

Preferably the outer layer is a compression garment according to the first aspect above.

In another aspect the invention provides a fabric, including: a moisture absorbent material forming at least predominantly a first surface of the single fabric layer; and a wicking material forming at least predominantly a second surface of the single fabric layer; wherein the fabric is knitted or woven from threads of at least the moisture absorbent and wicking materials.

Preferably the moisture absorbent material is composed of fibres having a hydrophilic core and a hydrophobic surface.

Preferably the moisture absorbent material is also a temperature regulating material. Preferably the moisture absorbent material is also an odour-inhibiting material.

Preferably the moisture absorbent material is also an anti-microbial material.

Preferably the moisture absorbent material is a natural material. Preferably the natural material is wool. Preferably the natural material is merino wool.

Preferably the moisture absorbent material has an average fibre diameter in the range 13 to 23 µm.

Preferably the wicking material is composed of fibres having a hydrophilic surface and low moisture absorption.

Preferably the wicking material is an abrasion resistant material.

Preferably the wicking material is a synthetic material. Preferably the wicking material is polyester, nylon or polypropylene.

Preferably the ratio of absorbent material to wicking material by weight is in the range 1:3 to 3:1.

Preferably the single fabric layer further includes an elastic material.

Preferably the elastic material is in the form of elastic thread.

Preferably the elastic material is elastane.

Preferably the elastic material is contained within the single fabric layer without being exposed on either the first or second surface.

Preferably the elastic material forms up to 50% of the weight of the single fabric layer.

Preferably the single fabric layer is knitted from threads of at least the first and second materials. Preferably the single fabric layer is knitted as a flat fabric layer. Alternatively the single fabric layer may be formed in an integral knitting process.

Preferably the first surface is formed by a first set of knit stitches formed predominantly from the moisture absorbent material and the second surface is formed by a second set of knit stitches formed predominantly from the wicking material.

Preferably a set of tuck stitches links the knit stitches.

In a further aspect the invention provides a two-layer compression garment system including: an inner fabric compression layer configured, in use, to apply a first predetermined level of compression; and two or more outer fabric compression layers, each configured, in use, to be applied directly over the inner fabric compression layer, each providing a different predetermined level of compression; such that the inner fabric compression layer and a selected one of the two or more outer fabric compression layers can be applied in order to achieve a desired cumulative level of compression.

In another aspect the invention provides a compression garment formed as a single fabric layer, including: a moisture absorbent material forming at least part of an inner surface of the single fabric layer; and a wicking material forming at least part of an outer surface of the single fabric layer; wherein the single fabric layer is knitted or woven from threads of at least the first and second materials.

In a further aspect the invention provides a compression garment including a fabric body and one or more touch markers positioned and arranged to assist correct alignment of the garment.

BRIEF DESCRIPTION OF THE DRAWINGS

The invention will now be described by way of example only, with reference to the accompanying drawings, in which:

FIG. 1 is a side view of a compression garment according to one embodiment;

FIG. 2A is a side view of a further compression garment;

FIG. 2B is a side view of a further compression garment;

FIG. 2C is a side view of a further compression garment;

FIG. 3 is a side view of a compression garment system in a first configuration;

FIG. 4 is a rear view of the compression garment system of FIG. 3;

FIG. 5 is a side view of the compression garment system of FIG. 3, in a second configuration;

FIG. 6 is a rear view of the compression garment system of FIG. 5;

DETAILED DESCRIPTION

Figure 7:
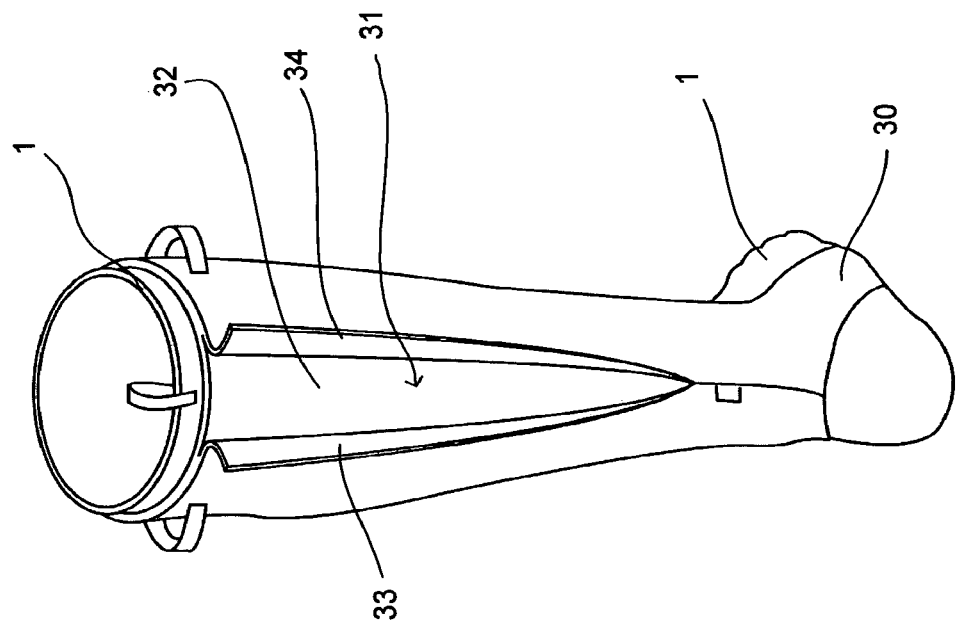
FIG. 7 is a perspective view of a compression garment system according to a further embodiment.

FIG. 1 shows a compression garment 1 in the form of the stocking. This garment can be used on its own to provide a level of compression, or may form an inner layer of a multilayer compression garment system, as discussed below.

The compression garment 1 is dimensioned and shaped to provide a desired level of compression when applied to a wearer's lower leg. The garment 1 also preferably provides a desired variation of compression over the garment, with maximum compression around the ankle and the level of pressure gradually reducing over the upper part of the garment 1. Generally the level of pressure provided by a graduated pressure garment may be greater towards the extremity.

The compression garment 1 is selected for or by a wearer based on sizing information or a measurement of a body part. For example, the appropriate size of garment 1 may be selected based on a measurement of the wearer's ankle.

The compression garment is formed from a fabric body 2. The fabric body is preferably formed as a single fabric layer as described below.

The garment 1 may include a number of handles or loops 3 which help a user to apply the garment 1. In the example shown a loop 3 is positioned at the top of the garment 1 and can be pulled by the wearer to assist in putting on the garment 1.

The garment may also include a number of touch markers 5, 6. These are markers arranged to be detected by touch. This is particularly advantageous because many wearers requiring compression therapy have failing vision due to age or underlying health problems. The touch markers 5, 6 help those wearers to properly align the garment 1. The touch markers 5, 6 may be separate components, such as plastic components applied to the fabric body 2, or a fabric solution such as raised stitching may be formed as part of the fabric body. The touch markers 5, 6 may provide information in addition to their position. For example, different touch marker patterns could be used for compression garments of different compression classes or sizes, providing a non-visual indication of class or size. The touch markers may also be visible markers (for example raised coloured stitching).

FIGS. 2A, 2B and 2C show three different compression garments 10, 11, 12. Each compression garment could be applied as a standalone garment, but preferably the garments of FIGS. 2A to 2C are used as part of a multilayer compression garment system. In one embodiment the garment of any one of FIGS. 2A to 2C is used as an outer compression layer over an inner compression layer formed by the garment of FIG. 1. When used in this way, the inner garment 1 may have a low fabric-to-fabric coefficient of friction to ease application of the outer layer over the inner layer.

In one embodiment each of the garments may be constructed, dimensioned and/or shaped so as to provide a different level of compression. For example, a compression garment system may provide the following compression options. Applying the garment of FIG. 1 alone provides Class A compression (i.e. 10 to 15 mmHg). Applying the garment of FIG. 1 as an inner layer, with the garment of FIG. 2A as an outer layer provides Class 1 compression (i.e. 16 to 21 mmHg). Applying the garment of FIG. 1 as an inner layer, with the garment of FIG. 2B as an outer layer provides Class 2 compression (i.e. 22 to 30 mmHg). Applying the garment of FIG. 1 as an inner layer, with the garment of FIG. 2C as an outer layer provides Class 3 compression (i.e. 34 to 46 mmHg). Thus the Applicant's compression garment system provides a range of options using the same inner layer with an outer layer chosen for the degree of compression required by the wearer.

The garments of FIGS. 2A, 2B and 2C are generally of similar configuration, so only FIG. 2A will be discussed further. The garment 10 includes a lower portion 14 which receives a user's foot and ankle. This portion may have a toe opening 15 and a heel opening 16, which reduces the amount of material around the foot and, for some users, may make it easier to apply the garment. The garment 10 also includes an upper portion 17 shaped to fit around a wearer's lower leg or calf region. Again, handles or loops 18 may be provided to help a wearer to pull the garment on. Touch markers 19 help the wearer to correctly align the garment 10.

The compression garment system including the inner garment 1 and choice of outer garments 10, 11, 12 may be provided in a range of sizes.

FIGS. 3 and 4 show the garment 10 with a zip closure 21 in an open position. The garment 10 includes an opening 22 which can be closed by the closure 21. The opening may extend all the way to the top edge of the garment 10. The opening is shown at the rear of the garment, which may provide easy access to the closure. However, the opening could be positioned at any suitable position around the garment 10.

Although the drawings show a zip closure, other suitable closures could be used, including hook and loop fasteners, domes, snap fasteners, buckles and/or releasable adhesive. Where a zip closure is used a loop or handle 23 may be positioned below the zip. Pulling on this loop or handle helps to straighten the line of the zip, which makes it easier to do up the zip.

FIGS. 5 and 6 show the garment 10 with the zip closure 21 in a closed position. In this position the closure provides a fixed connection between the two sides 25, 26 of the opening 22. In the closed position the shaped fabric body 28 of the garment 10 provides a first predetermined level of compression.

FIG. 7 shows a further embodiment in which a compression garment 30 includes an opening 31 which can be closed by a zip fastener or other closure (not shown in FIG. 7). A panel or band of elastic material 32 extends across the opening, being attached at or near the two sides 33, 34 of the opening 31. The elastic material may extend over the entire length of the opening, as shown in FIG. 7, or a band (of e.g. 5 to 10 cm in width) could be used near the top of the opening. Alternatively a number of bands of elastic material could be distributed along the length of the opening.

Figure 8:
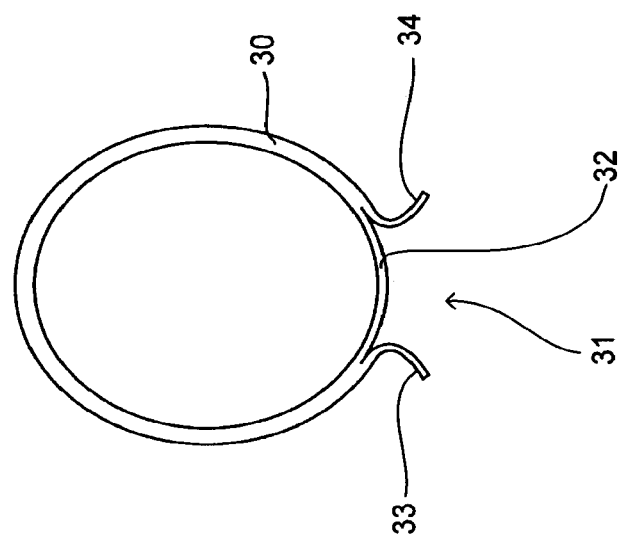
FIG. 8 is a sectional view through part of the compression garment system of FIG. 7.

This structure is clearly shown in FIG. 8, which is a sectional view through the garment 30. This structure may be used in the garment of any one of FIGS. 2A to 6. The garment may be a standalone compression garment or part of a multilayer compression system, as shown in FIG. 7.

The elastic material 32 tends to draw the two sides 33, 34 of the opening together when the closure is in an open position. This elastic material helps to bring the sides of the closure together, which makes it easier to close the closure. When the closure is closed, the elastic material contracts so as to lie flat under the fabric body of the garment 30. This is important for comfort and safety, since fabric bunching under the fabric body could irritate the skin, cause a pressure point, or even interfere with the circulatory system.

In addition, the elastic material can be used to provide a second predetermined level of compression. So, the compression garment 30 has two alternative, functional configurations. In one configuration the closure is closed and the fabric body of the garment provides a first predetermined level of compression. In a second configuration the closure is open and the elastic material 32 together with the fabric body of the garment 30 provides a second predetermined level of compression. This is particularly advantageous because a wearer can partially release the compression pressure by opening the closure. Wearers are often required to wear compression bandages or garments for a long period of time, and this feature provides for some relief through temporary and partial release of the pressure without removing the garment. In one example, the second level of pressure is around 4 to 12 mmHg less than the first level of pressure, preferably around 6 mmHg less than the first level of pressure.

The Applicant has developed new fabrics. These fabrics may provide improved performance in compression garments and in multi-layer compression garment systems.

The new fabrics provide excellent compression properties while also regulating the skin environment of the user. This regulation provides an excellent environment for healing of any wounds or lesions on the skin underneath the compression garment. The garment may regulate moisture levels and/or temperature of the skin environment. This regulated skin environment provides a healthy, natural environment in which the skin can function as well as possible. This provides two important advantages. First, good conditions are provided for healing of existing wounds or lesions. Second, the skin is given the best chance of resisting development of further skin conditions. This is particularly important for patients with poor blood flow because small skin problems can rapidly worsen (especially where skin conditions are poor, as they are beneath many prior compression systems).

Regulation is provided partly through the use of absorbent materials and partly through the use of wicking materials.

In this specification the term "absorbent" refers to a material capable of absorbing moisture vapour and subsequently releasing or desorbing that moisture vapour to the surrounding environment. The term "wicking" refers to a material with low absorption of moisture, but which will transport liquid moisture by capillary action or some other suitable mechanism.

The absorbent and wicking materials may be processed by knitting or weaving or other suitable process into a single fabric layer including both materials. Preferably the single fabric layer is formed such that one surface (which will be the inner surface of the compression garment) is formed predominantly by the absorbent material, while the other surface (which will be the outer surface of the compression garment) is formed predominantly from the wicking material. This allows the absorbent material to be in contact with the skin while the wicking material is separated from the skin.

In such a fabric, liquid moisture in the skin environment is wicked away from the skin by the wicking material. Moisture vapour (e.g. water vapour) is absorbed by the absorbent material and then released from the absorbent material away from the skin. Thus both moisture vapour and liquid moisture are effectively removed from the skin environment.

Where merino wool or a similar material is used as the absorbent material, moisture vapour is absorbed (into the wool's hydrophilic interior) from the high-humidity skin environment and is released (desorbed, or diffused) to the external environment. A porous synthetic outer garment does not prevent this diffusion because it does not interact with moisture vapour and is a porous knit structure.

Liquid moisture does not readily adhere to the surface of merino wool or similar materials due to the hydrophobic exterior of the wool fibres. The wicking material therefore pulls liquid moisture through the fabric to the outside of the garment where it can evaporate.

Thus, the fabric is generally a bi-component fabric constructed from two fibre types having distinct physical and chemical properties. The differing moisture absorbency and wicking behaviours of the two fibres means that moisture will be drawn through the structure to the outside where it can evaporate, keeping the skin dry.

The two fibre types are placed separately in the fabric structure, for example by placing one fibre type exclusively or predominantly on one side of the fabric, and placing the other fibre type exclusively or predominantly on the other side. Alternatively the two fibre types can be combined in an alternating stripe configuration.

In one embodiment the absorbent material is merino wool. Merino wool and its natural thermoregulatory properties provide excellent next-to-skin comfort.

However, other suitable materials may be used for the absorbent material, including natural materials, wool, or even synthetics providing the properties required. Increasingly synthetic fibres are being developed to mimic the properties of natural fibres (including wool and merino wool) and such fibres are intended to fall within the scope of the invention.

The absorbent material may be a hygroscopic material. The absorbent material may be composed of fibres having a hydrophilic core and a hydrophobic surface. The moisture absorbent material may be a temperature regulating material. The moisture absorbent material may also be an odour-inhibiting material. These properties are all provided by wool, and particularly by merino wool.

The moisture absorbent material may have anti-microbial properties. It is believed that wool, and particularly merino wool, may have anti-microbial properties. Other fabrics may be modified to have anti-microbial properties, for example by the addition of antimicrobial agents.

Merino wool has been shown to have naturally effective resistance to odour build-up. Merino wool absorbs and traps odours; and has surface properties inhospitable to microbial growth. Other fibres need to be modified (such as by the addition of antimicrobial agents) to be odour retardant.

Such properties are advantageous for next to skin surfaces where wound healing is a factor.

The moisture absorbent material may have an average fibre diameter in the range 13 to 23 μm (provided by most merino wool) but preferably has a diameter less than 19 μm for excellent next-to-skin comfort.

The moisture absorbent material may have a standard regain of around 10 to 20%, with merino wool providing a standard regain around 17%. Regain is the moisture content as a percentage of the fibre's dry weight. Standard regain is measured at 20° C. and 65% relative humidity and is an indication of the moisture buffering capability of the fibre, higher standard regain means greater buffering capability.

The moisture absorbent material may have a saturation regain of around 30 to 40%, with merino wool providing a saturation regain of around 35%. Saturation regain is measured at 100% relative humidity. This is another indication of the moisture buffering capability of the fibre; specifically it indicates how much moisture it can hold before feeling damp.

The moisture absorbent material may have a thermal conductivity greater than 160 mW/m/K, preferably around 160 to 240 mW/m/K, with merino wool providing a thermal conductivity of around 193 mW/m/K. Thermal conductivity is a measure of how easily heat flows through a material. Lower conductivity means better insulation but fibre thermal conductivity is only one factor in overall fabric insulation (trapping air is of greater significance). Wool has lower thermal conductivity than its main hosiery competitors: cotton and nylon (the latter being the usual fibre type used in compression hosiery). The natural crimp of merino wool helps it to trap air.

The moisture absorbent material may have a limiting oxygen index (LOI) greater than 21, preferably around 24 to 26, with merino wool providing an LOI of around 25. LOI is a measure of flammability and is defined as the volume percentage of oxygen in a nitrogen/oxygen mixture that will just permit burning. The volume percentage of oxygen in air is 21%, so materials having an LOI greater than this will not sustain burning in air. Merino wool's LOI is >21, so it will not sustain burning.

Static electricity build up in apparel situations is usually a minor inconvenience to the wearer. Merino wool has inherently low static build up, thought to be due to its relatively high moisture content. Synthetic fibres (having low moisture content) are more prone to static build-up, and may need special chemical treatments to reduce this.

Merino wool has a fibre density within the range of the other commonly-used fibre types.

The wicking material may be composed of fibres having a hydrophilic surface and low moisture absorption. The wicking material may be an abrasion resistant material.

Synthetic materials may be suitable for the wicking material, including polyester, nylon or polypropylene.

The absorbent material and the synthetic material may be combined in any suitable proportion, but generally a ratio of absorbent material to wicking material by weight between 1:3 and 3:1 is expected to provide satisfactory performance.

In one embodiment the fabric is a knitted fabric, such as a two face, single jersey knitted fabric. However, it may be possible to form the fabric by weaving or some other process.

The fabric may be weft-knitted on a circular knitting machine of gauge greater than 20 needles per inch (double jersey) and 26 needles per inch (single jersey).

During knitting an elastic material such as elastomeric fibre (e.g. elastane or spandex) may be knitted with some or all of the other yarns or otherwise introduced into the fabric layer. Elastane is a fibre of greater than 85% polyurethane, with extremely high extension at breaking point (more than 200%) and good elastic recovery.

The elastane yarn may be positioned such that it lies inside the plane of the fabric, and is not exposed on either face. The elastane is knitted in such a way to provide maximum stretch and recovery to the fabric, allowing it to be used in medical or sports applications to provide beneficial levels of mechanical compression to the body of the wearer. While the fabric without elastane provides some compression, the level of this compression would creep over time and the fabric would most likely not recover well after use. The elastane also helps to "pull in" the fabric during manufacture so that the finished fabric is capable of a large amount of extension.

The elastic material may form up to 50%, preferably 20 to 35%, of the weight of the single fabric layer. The finished fabric may have a maximum extension between 35 and 55% by length.

The Applicant's material shows improved recovery properties over prior compression garment materials. In particular, the Applicant's fabric has a strong tendency to dimensionally recover during laundering, which helps to return the compression garments back to their original size, or close to that size. All compression garments tend to stretch and extend in circumference during use, and if there is insufficient recovery after removal of the garment the unextended size of the garment will gradually increase and the level of compression provided will gradually decrease. In other words, there can be a residual extension when the load is removed.

In contrast to prior garments, when the Applicant's garment is washed, it returns strongly to its original size so the wearer receives the designed level of compression. In other words, the Applicant's garment will function as designed for a greater number of wash cycles, and therefore over a longer useful life, than prior garments. The Applicant believes this is at least partly due to the use of wool, particularly merino wool, in the fabrics discussed herein. In particular it is believed that any temporary deformation of fibres (bending or stretching) caused by stretching the fabric is relaxed by wet laundering. This improved recovery means that the garment can provide the intended physiological benefit to the user over a longer period of time.

The Applicant has tested its product against existing compression products. Results of that testing are shown in the following table. Product A is a commercially available sock intended for use on long flights etc and formed from 93% polyamide material with designed compression around 14 to 17 mmHg. Product B is a commercially available medical support stocking formed from 69% polyamide material with designed compression around 30 mmHg. Product C is a commercially available sports sock formed from 91% polyamide material with designed compression around 18-25 mmHg. The basic composition in all cases is nylon with an elastomeric fibre (referred to in this document by the generic term 'elastane') included to provide the compressive force and stretch/recovery behaviour. The amount of elastane present is relatively high, as expected for a product offering therapeutic levels of compression.

This testing involved taking a section from the lower section of each garment. That section was put under load (to a designated size) every day for eight hours. The garment was laundered once a week. The percentages given in the table are calculated as $100(s1-s2)/s1$, where s1 is the size of garment before washing and s2 is the size of garment after washing. These figures show that the Applicant's garment recovers strongly on washing over a prolonged period.

|  | Product A | Product B | Product C | Applicant's garment |
| --- | --- | --- | --- | --- |
| Week 1 | — | — | — | — |
| Week 2 | 7.3% | 4.1% | 8.8% | 13.9% |
| Week 3 | 9.7% | 6.3% | 10.8% | 15.3% |
| Week 4 | 12.3% | 6.7% | 13.1% | 19.7% |
| Week 5 | 11.3% | 7.9% | 13.8% | 19.5% |
| Week 6 | 12.2% | 6.0% | 13.0% | 17.9% |
| Week 7 | 10.5% | 7.3% | 11.1% | 17.4% |
| Week 8 | 12.2% | 7.9% | 12.7% | 20.8% |
| Week 10 | 12.1% | 7.8% | 12.7% | 21.6% |
| Week 11 | 11.8% | 9.6% | 11.5% | 19.3% |
| Week 12 | 11.0% | 7.4% | 12.4% | 19.2% |
| Week 13 | 13.7% | 7.2% | 11.9% | 21.0% |
| Week 14 | 12.2% | 7.3% | 12.7% | 18.9% |
| Week 15 | 10.4% | 9.3% | 12.7% | 20.2% |
| Week 16 | 12.9% | 7.9% | 12.6% | 19.7% |
| Week 17 | 12.2% | 7.9% | 11.8% | 21.8% |
| Week 18 | 11.9% | 8.1% | 12.4% | 20.8% |
| Week 20 | 11.3% | 7.3% | 12.7% | 16.5% |
| Mean | 11.5% | 7.4% | 12.2% | 19.0% |

Testing has been conducted as to the effects of the Applicant's graduated compression stockings on lower limb venous haemo-dynamics in seated adults with normal peripheral circulation. The study is a randomised controlled Doppler Ultrasound trial comparing one limb with the stocking applied, to the other limb with no stocking applied (control).

The primary outcome is an improvement in peak venous velocity in the popliteal vein, in participants seated over a 120 minute timeframe, while wearing an Encircle below-knee merino graduated compression stocking, compared with not wearing a stocking.

In addition, there is improvement in mean venous velocity, vein diameter, total volume flow in the popliteal vein, and size (circumference) and shape of the limb, in participants seated over a 120 minute timeframe, while wearing an Encircle below-knee merino graduated compression stocking, compared with not wearing a stocking.

The fabric may be processed, e.g. through a scour treatment (textile washing process), in order to remove any residues, such as grease or processing lubricants that are present during the knitting or yarn spinning process and then Santex dried.

Figure 9:
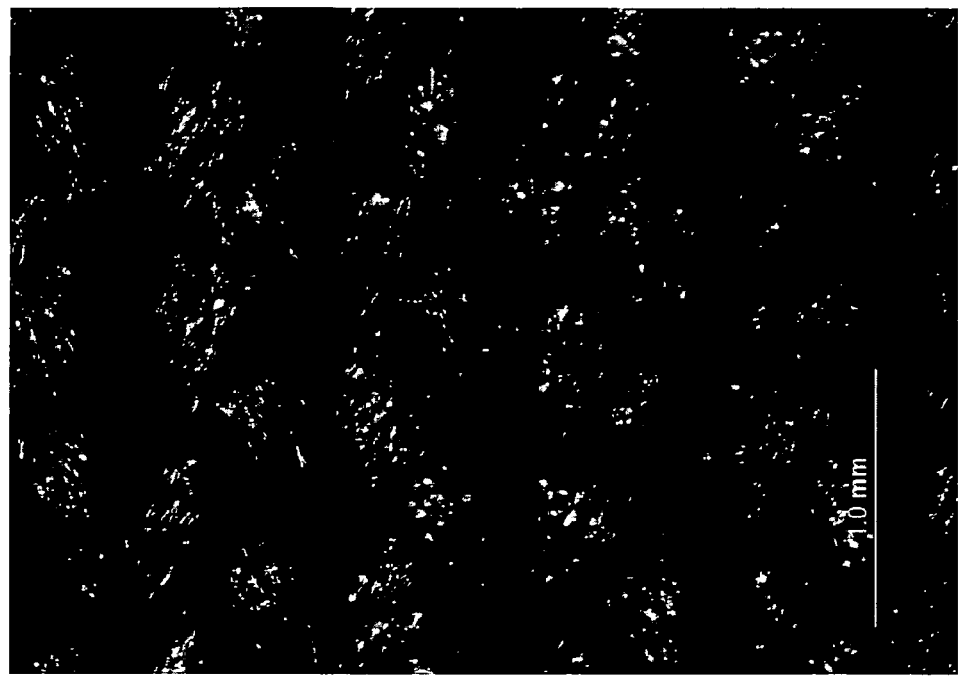
FIG. 9 shows one surface of a fabric.
Figure 9A:
FIG. 9A shows the other surface of the fabric of FIG. 9.

FIGS. 9 and 9A show first and second faces of a fabric formed from merino wool and a synthetic wicking material. FIG. 9 shows one face, formed by stitches of the synthetic wicking material. FIG. 9B shows the other face, formed by stitches of the merino wool.

Figure 10:
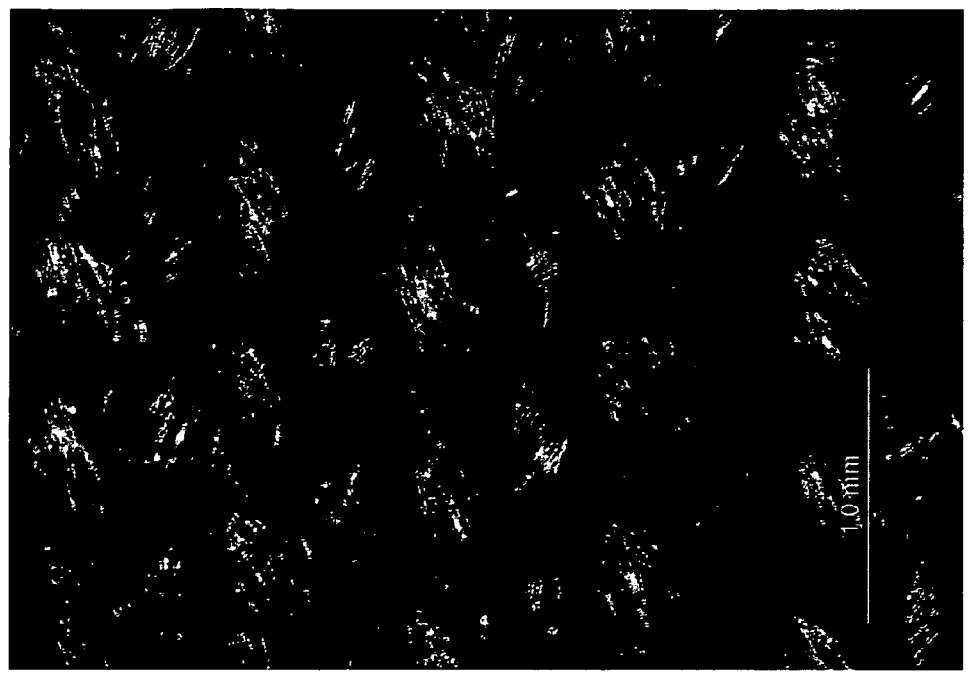
FIG. 10 shows one surface of another fabric.
Figure 10A:
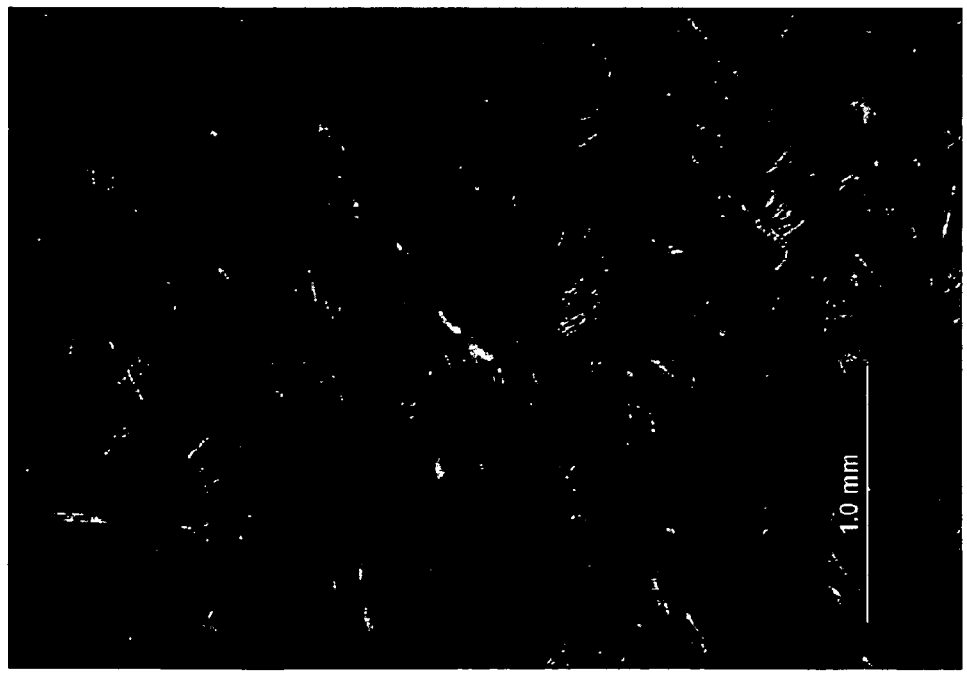
FIG. 10A shows the other surface of the fabric of FIG. 10.

FIGS. 10 and 10A show first and second faces of a further fabric. In this example, a double jersey fabric has been constructed where merino wool yarns (14 tex, 19 µm mean fibre diameter) are knitted just to one side of the structure (all knit on the dial needles) and a branded polyester multifilament (ADVANSA Thermo° Cool™, 83 decitex, 72 filaments) is knitted to the other side of the structure (all knit on the cylinder needles). The two layers are then linked together to form a single fabric by tucking alternating dial and cylinder needles with additional Thermo° Cool™ yarn. A 78 decitex branded elastane (Invista Elaspan®) is knitted on the dial and cylinder stitches (but not the alternating dial and cylinder tuck stitches used to hold together the merino and the Therm° Cool™ layers).

Thus the inner surface is formed by a first set of knit stitches formed at least predominantly from the moisture absorbent material and the outer surface is formed by a second set of knit stitches formed at least predominantly from the wicking material, with a set of tuck stitches linking the knit stitches.

Thermo° Cool™ polyester is a multifilament synthetic yarn, which contains both flat channelled fibres and round hollow-core fibres. The flat channelled fibres have high relative surface area and wick sweat and moisture away from the skin to the fabric's surface where it can evaporate, while the hollow fibres trap air in the centre of the fibre for improved insulation.

Keeping the polyester and the merino components on separate sides of the fabric structure gives benefits in terms of comfort and performance.

Performance of the resultant fabric would be described as heavy-weight with maximum stretch and powerful recovery due to it being processed at temperatures below that which would set the elastane (which occurs at 190° and above). However, other forms of fabric may be suitable, including light-weight materials and materials with lower stretch.

Figure 11:
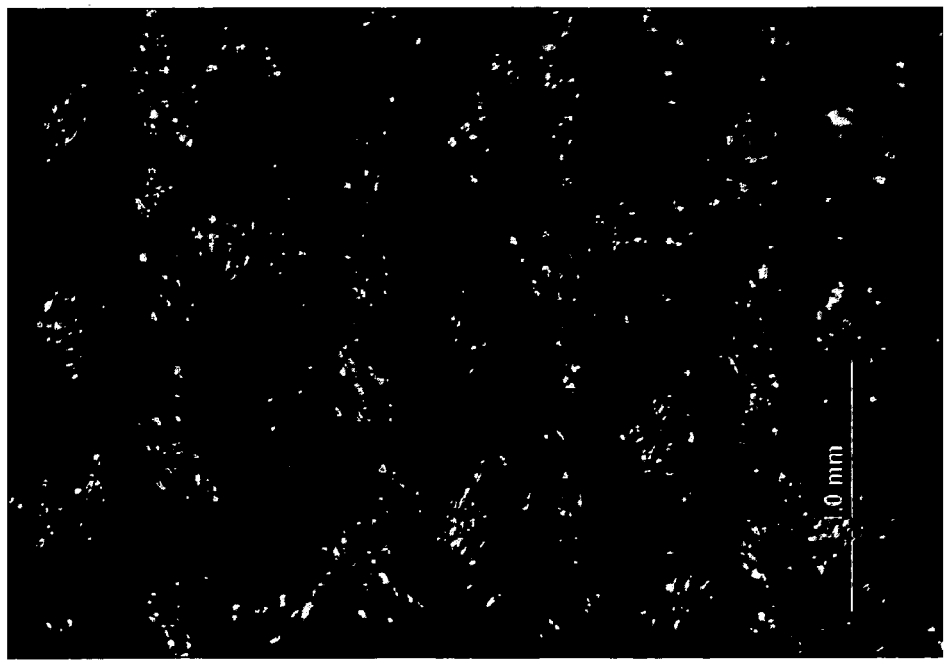
FIG. 11 shows one surface of a further fabric.
Figure 11A:
FIG. 11A shows the other surface of the fabric of FIG. 11.

FIGS. 11 and 11A show the two faces of a further example fabric.

Figure 12:
FIG. 12 shows one surface of yet another fabric.
Figure 12A:
FIG. 12A shows the other surface of the fabric of FIG. 12.

FIGS. 12 and 12A show the two faces of yet another example fabric.

Figure 13:
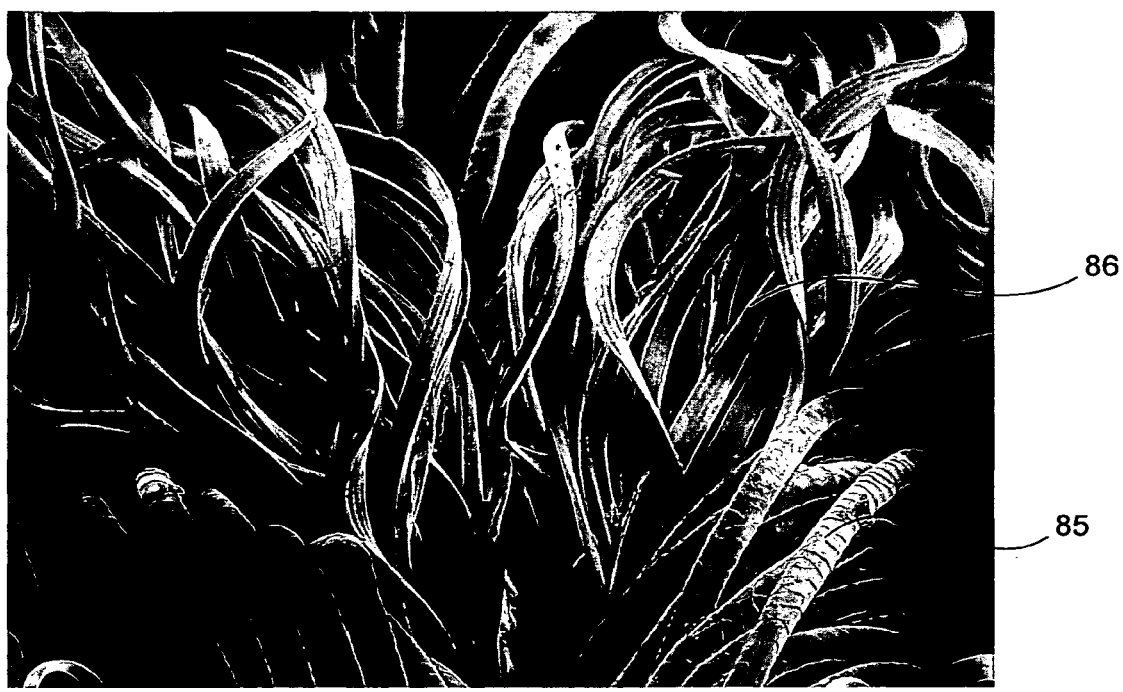
FIG. 13 is a Scanning Electron Microscope image of one embodiment of the Applicant's fabric, showing wool and synthetic fibres.

FIG. 13 is a Scanning Electron Microscope image showing the structure of one embodiment of the Applicant's fabric. Here the separate groupings of merino fibres 85 and synthetic fibres 86 can clearly be seen.

Any of these fabrics may be used to form any of the compression garments described in this specification.

The single fabric layer may either be knitted as a flat fabric layer and then processed to form the finished compression garment, or may be formed by an integral knitting process which essentially results in the finished garment. Any of the compression garments described in this specification could be formed in either of these ways.

In a multilayer compression garment system the inner layer is preferably formed from a fabric as described above. Outer layers may also be formed from these fabrics, but could be of different fabrics. Preferably if another fabric is used it should at least include a wicking material so that liquid moisture can be effectively wicked to the outside of the garment system.

In a two-layer system liquid moisture wicked through the inner layer as discussed above will be wicked from the interface between the inner and outer layers through the outer layer where it can evaporate. Moisture vapour released from the absorbent material in the inner layer may either pass through a porous outer layer or, if absorbent material is also provided in the outer layer, be absorbed and released by that material to the outside of the garment system, in a similar manner to that discussed above.

Note that extreme conditions (in particular where the external environment has extremely high humidity) the absorption/desorption of moisture vapour and the evaporation of moisture from the outside of the garment or garment system may be diminished or may not work effectively. However, in normal conditions the garments and garment systems are designed to function as described above.

Although the Applicant's garments have been described with reference to compression garments for the lower leg, compression garments for other parts of the body also fall within the scope of the invention.

The Applicant's fabrics provide good compression characteristics, with the ability to create compression garments providing specific compression levels. The structure of the fabrics and the materials used provide an excellent skin environment, in which moisture and temperature levels are kept at satisfactory levels. This helps with the healing of wounds or lesions and also provides a more comfortable compression garment. Comfort is especially important since these types of garment must be worn for long periods of time.

Particularly where merino wool or similar materials are used in conjunction with wicking materials, both water vapour and liquid moisture can be effectively removed from the skin environment while the wool also assists in regulating the temperature of that environment.

The Applicant's garments and garment systems are also relatively easy to apply. The garments are designed for application by older or weaker patients without professional assistance, at least up to class 2 compression. This is achieved by a layered system in which compression is provided by two or more garments which can be separately applied. Older or weaker patients will find it easier to apply two layers each providing part of the required compression, which builds up the total level of pressure applied, than a single, much firmer, layer providing the entire compression.

The garments may also be provided with handles or loops to assist with application and with touch markers to assist with alignment.

At higher compression levels professional assistance may be required for application of an outer garment. However, application is still expected to be easier and faster than for many prior compression systems. In any case, compression therapy at higher compression levels is required to be supervised by healthcare professionals.

The design of the outer garment, with an opening and closure also assists application, since only the lower part of the garment need be pulled forcefully over the patient's foot. The upper portion, with the closure in an open position, has a large diameter and is relatively easily pulled over the foot and positioned around the calf. The elastic material attached across the opening both assists with closing the closure and importantly provides a second designed level of compression. A wearer can temporarily reduce the compression pressure by releasing the closure. A lesser level of compression is applied until the closure is closed again. So there is no need to remove the entire garment in order to obtain some temporary relief.

While the present invention has been illustrated by the description of the embodiments thereof, and while the embodiments have been described in detail, it is not the intention of the Applicant to restrict or in any way limit the scope of the appended claims to such detail. Additional advantages and modifications will readily appear to those skilled in the art. Therefore, the invention in its broader aspects is not limited to the specific details, representative apparatus and methods, and illustrative examples shown and described. Accordingly, departures may be made from such details without departure from the spirit or scope of the Applicant's general inventive concept.

The invention claimed is:

1. A multi-layer compression garment system, comprising:
an inner layer compression garment configured to encompass a wearer's lower leg to apply a predetermined level of compression to the wearer's lower leg, wherein the inner layer compression garment includes a fabric body, a closed toe, and a closed heel; and
a standalone outer compression garment configured to be applied over the inner layer compression garment, the standalone outer compression garment comprising:
a shaped fabric body with a toe opening, a heel opening, and an opening configured to extend along the length of a wearer's lower leg, wherein the shaped fabric body is formed as a fabric layer that includes an elastic material;
a closure on a back of the standalone outer compression garment configured to open and close the opening; and
at least one panel or band of elastic material on the back of the standalone outer compression garment that spans the opening and tends, in use, to draw the two sides of the opening together when the closure is in an open position;
wherein, in use, the standalone outer compression garment, via at least the elastic material in the fabric layer, provides a first predetermined level of compression to the wearer's lower leg when the closure is positioned such that the opening is closed and the fabric layer extends around the perimeter of the wearer's lower leg,
wherein, in use, the standalone outer compression garment, via at least the elastic material in the fabric layer and the at least one panel or band of elastic material, provides a second predetermined level of compression when the closure is positioned such that the opening is open and the least one panel or band of elastic material extends across the opening, and
wherein the second predetermined level of compression is less than the first level of predetermined compression.

2. The multi-layer compression garment system of claim 1, wherein at least a Class 1 compression of at least 16 mmHg is provided by applying the inner layer compression garment with the standalone outer compression garment.

3. The multi-layer compression garment system of claim 2, wherein the second predetermined level of compression is at least 4 mmHg less than the first predetermined level of compression.

4. The multi-layer compression garment system of claim 1, wherein the opening extends to a top edge of the standalone outer compression garment.

5. The multi-layer compression garment system of claim 1, wherein the at least one panel or band of elastic material lies flat underneath the shaped fabric body when the closure is positioned such that the opening is closed.

6. The multi-layer compression garment system of claim 1, wherein the closure provides a fixed connection between the sides of the opening when the opening is closed.

7. The multi-layer compression garment system of claim 1, wherein the closure is a zip closure.

8. The multi-layer compression garment system of claim 1, wherein the shaped fabric body includes a lower portion configured to fit around the wearer's foot and an upper portion including the opening, the at least one panel or band of elastic material, and the closure.

9. The multi-layer compression garment system of claim 1, wherein the standalone outer compression garment further comprises one or more handles or loops to assist with at least one of the actions of: application of the standalone outer compression garment, closing of the closure, or opening of the closure.

10. The multi-layer compression garment system of claim 1, wherein the elastic material in the fabric layer comprises elastomeric fibers.

11. A multilayer compression garment system, comprising:
an inner layer compression garment configured to encompass a wearer's lower leg to apply a predetermined level of the compression to the wearer's lower leg, wherein the inner layer compression garment includes a fabric body, a closed toe, and a closed heel; and
two or more standalone outer fabric compression garments comprising:
a first standalone outer compression garment configured to be applied over the inner layer compression garment, the first standalone outer compression garment comprising:
a first shaped fabric body with a first toe opening, a first heel opening, and a first opening configured to extend along the length of the wearer's lower leg, wherein the first shaped fabric body is formed as a first fabric layer that includes an elastic material;
a first closure on a back of the first standalone outer compression garment configured to open and close the first opening; and
at least one panel or band of elastic material spanning the first opening and tending, in use, to draw the two sides of the first opening together when the first closure is in an open position;
wherein, in use, the first standalone outer compression garment, via at least the elastic material in the first fabric layer, provides a first predetermined level of compression to the wearer's lower leg when the first closure is positioned such that the first opening is closed and the first fabric layer extends around the perimeter of the wearer's lower leg, and
wherein, in use, the first standalone outer compression garment, via at least the elastic material in the first fabric layer and the at least one panel or band of elastic material spanning the first opening, provides a second predetermined level of compression when the first closure is positioned such that the first opening is open and the least one panel or band of elastic material extends across the first opening; and
a second standalone outer compression garment configured to be applied over the inner layer compression garment, the second standalone outer compression garment comprising:
a second shaped fabric body with a second toe opening, a second heel opening, and a second opening configured to extend along the length of the wearer's lower leg, wherein the second shaped body is formed as a second fabric layer that includes the elastic material;
a second closure on a back of the second standalone outer compression garment configured to open and close the second opening; and
at least one panel or band of elastic material spanning the second opening and tending, in use, to draw the two sides of the second opening together when the second closure is in an open position;

wherein, in use, the second standalone outer compression garment, via at least the elastic material in the second fabric layer, provides a third predetermined level of compression to the wearer's lower leg when the second closure is positioned such that the second opening is closed and the second fabric layer extends around the perimeter of the wearer's lower leg, and wherein, in use, the second standalone outer compression garment, via at least the elastic material in the second fabric layer and the at least one panel or band of elastic material spanning the second opening, provides a fourth predetermined level of compression when the second closure is positioned such that the second opening is open and the least one panel or band of elastic material extends across the second opening, wherein, in use, the multilayer compression garment system provides a Class A compression when the inner layer compression garment is worn alone, a Class 1 compression when the inner layer compression garment is worn with the first standalone outer compression garment, and a Class 2 or Class 3 compression when the inner layer compression garment is worn with the second standalone outer compression garment.

12. The multilayer compression garment system of claim 11, wherein the second predetermined level of compression is at least 4 mmHg less than the first predetermined level of compression.

13. A multilayer compression garment system, comprising:

an inner layer compression garment configured to encompass a wearer's lower leg to apply a predetermined level of compression to the wearer's lower leg, wherein the inner layer compression garment is formed as a fabric layer with a moisture absorbent material forming an inner surface and a wicking material forming an outer surface, and wherein the inner layer compression garment includes a closed toe and a closed heel; and a standalone outer compression garment configured to be applied over the inner layer compression garment, wherein the standalone outer compression garment is formed as a fabric layer with a moisture absorbent material and a wicking material, and wherein the standalone outer compression garment comprises:

a shaped body with a toe opening, a heel opening, and an opening configured to extend along the length of the wearer's lower leg;

a closure configured to open and close the opening; and at least one panel or band of elastic material spanning the opening and tending, in use, to draw the two sides of the opening together when the closure is in an open position;

wherein, in use, the standalone outer compression garment is configured to provide a first predetermined level of compression to the wearer's lower leg when the closure is positioned such that the opening is closed and a second predetermined level of compression to the wearer's lower leg when the closure is positioned such that the opening is open, and wherein the second predetermined level of compression is less than the first predetermined level of compression.

14. The multilayer compression garment system of claim 13, wherein the predetermined level of compression provided by the inner layer compression garment alone is between 10 mmHg and 15 mmHg.

15. The multilayer compression garment system of claim 13, wherein the second predetermined level of compression is at least 4 mmHg less than the first predetermined level of compression.

16. The multilayer compression garment system of claim 13, wherein at least a Class 1 compression of at least 16 mmHg is provided by applying the inner layer compression garment with the standalone outer compression garment.

17. The multilayer compression garment system of claim 13, wherein, in use, the multilayer compression garment system provides a Class A compression when the inner layer compression garment is worn alone and a Class 1, Class 2, or Class 3 compression when the inner layer compression garment is worn with the standalone outer compression garment.

18. The multilayer compression garment system of claim 13, wherein the inner layer compression garment is a shaped compression garment.

19. The multilayer compression garment system of claim 13, wherein the closure is a zip closure.

* * * * *

UNITED STATES PATENT AND TRADEMARK OFFICE
CERTIFICATE OF CORRECTION

PATENT NO. : 12,195,893 B2  
APPLICATION NO. : 15/450735  
DATED : January 14, 2025  
INVENTOR(S) : Blythe Guy Rees-Jones et al.

It is certified that error appears in the above-identified patent and that said Letters Patent is hereby corrected as shown below:

In the Claims

Column 16, Claim 11, Line 55, cancel the text "...a second shaped fabric body with a second toe opening, a second heel opening, and a second opening configured to extend along the length of the wearer's lower leg, wherein the second shaped body is formed as a second fabric layer that includes the elastic material;"

Please insert the following: --...a second shaped fabric body with a second toe opening, a second heel opening, and a second opening configured to extend along the length of the wearer's lower leg, wherein the second shaped fabric body is formed as a second fabric layer that includes the elastic material;--

Column 18, Claim 13, Line 1, cancel the text ""...a shaped body with a toe opening, a heel opening, and an opening configured to extend along the length of the wearer's lower leg;"

Please insert the following: --...a shaped fabric body with a toe opening, a heel opening, and an opening configured to extend along the length of the wearer's lower leg;--

Signed and Sealed this  
First Day of April, 2025

Coke Morgan Stewart  
*Acting Director of the United States Patent and Trademark Office*